(12) United States Patent
Hockersmith et al.

(10) Patent No.: US 8,971,480 B2
(45) Date of Patent: Mar. 3, 2015

(54) SYSTEM AND METHOD FOR MOUNTING X-RAY TUBE ON A CT GANTRY FOR HIGH G-LOAD APPLICATIONS

(71) Applicant: General Electric Company, Schenectady, NY (US)

(72) Inventors: Ron Kent Hockersmith, Waukesha, WI (US); Michael Scott Hebert, Muskego, WI (US); Kenwood P. Dayton, Mequon, WI (US); Alexander Thomas Ryan, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 120 days.

(21) Appl. No.: 13/913,088

(22) Filed: Jun. 7, 2013

(65) Prior Publication Data

US 2014/0362969 A1 Dec. 11, 2014

(51) Int. Cl.
*G01N 23/00* (2006.01)
*H05G 1/02* (2006.01)
*G01N 23/04* (2006.01)

(52) U.S. Cl.
CPC ............. *H05G 1/02* (2013.01); *G01N 23/046* (2013.01)
USPC .......................................................... 378/15

(58) Field of Classification Search
CPC ...... A61B 6/0306; A61B 6/4085; A61B 6/56; G06T 11/003; G01N 23/046
USPC .............................................. 378/4, 9, 15, 193
See application file for complete search history.

(56) References Cited

U.S. PATENT DOCUMENTS

| | | | |
|---|---|---|---|
| 6,519,312 B1* | 2/2003 | Tybinkowski et al. | ............ 378/4 |
| 7,289,033 B2 | 10/2007 | Hockersmith | |
| 7,450,690 B2 | 11/2008 | Block et al. | |
| 7,519,157 B2 | 4/2009 | Hockersmith et al. | |
| 2009/0212472 A1* | 8/2009 | Adonakis | .................... 267/64.21 |
| 2010/0058602 A1* | 3/2010 | McMurtry | ...................... 33/503 |
| 2011/0142532 A1* | 6/2011 | Diemirbey | ...................... 403/56 |
| 2012/0039011 A1* | 2/2012 | Thiel et al. | .................... 361/131 |

* cited by examiner

*Primary Examiner* — Irakli Kiknadze
(74) *Attorney, Agent, or Firm* — Ziolkowski Patent Solutions Group, SC

(57) ABSTRACT

A mounting structure for mounting an x-ray tube on a CT rotatable gantry is disclosed. The mounting structure includes base plates that are boltable to the CT rotatable gantry and have bearing strut connections formed thereon. Spherical bearing struts are provided in the mounting structure to mechanically couple the x-ray tube to the base plates, with the spherical bearing struts each having a first end secured in a respective bearing strut connection of the x-ray tube casing and a second end secured in a respective bearing strut connection of the base plates. The spherical bearing struts constrain a gantry-load direction displacement of the x-ray tube and enable rotation and displacement of the x-ray tube around at least one axis of rotation or in one direction other than a gantry load direction, so as to accommodate thermal displacements in the x-ray tube created during operation thereof.

20 Claims, 8 Drawing Sheets

SYSTEM AND METHOD FOR MOUNTING X-RAY TUBE ON A CT GANTRY FOR HIGH G-LOAD APPLICATIONS

BACKGROUND OF THE INVENTION

Embodiments of the invention relate generally to computed tomography (CT) imaging and, more particularly, to a method and apparatus for mounting an x-ray tube on a CT gantry assembly for use in high g-load applications.

Computed tomography (CT) imaging systems typically include an x-ray tube, a detector, and a gantry assembly to support the x-ray tube and the detector. In operation, an imaging table, on which an object is positioned, is located between the x-ray tube and the detector. The x-ray tube typically emits radiation, such as x-rays, toward the object. The radiation typically passes through the object on the imaging table and impinges on the detector. As radiation passes through the object, internal structures of the object cause spatial variances in the radiation received at the detector. The detector converts the received radiation to electrical signals and then transmits data received, and the system translates the radiation variances into an image, which may be used to evaluate the internal structure of the object. One skilled in the art will recognize that the object may include, but is not limited to, a patient in a medical imaging procedure and an inanimate object as in, for instance, a package in an x-ray scanner or computed tomography (CT) package scanner.

A typical x-ray tube includes a cathode that provides a focused high energy electron beam that is accelerated across a cathode-to-anode vacuum gap and produces x-rays upon impact with an active material or target provided. Because of the high temperatures generated when the electron beam strikes the target, typically the target assembly is rotated at high rotational speed for purposes of cooling the target. Components of the x-ray tube are placed in a ultra-high vacuum which is maintained by a frame that is typically made of metal or glass.

In recent years, it has been desired within the CT industry to increase gantry speeds to greater than 0.27 seconds per gantry rotation. As the industry drives to faster gantry speeds, the mechanical loading on x-ray tubes has increased as well. Generally the mechanical loading on an x-ray tube increases as the square of the gantry rotational speed, thus increased gantry speeds have lead to enormous g-loading on the x-ray tube. Going forward, state-of-the-art CT systems may require gantry speeds that impart loads of much greater than 40 g's or more to the x-ray tube, thereby still further increasing the mechanical loading on the x-ray tube.

At such speeds and associated loads, proper constraining of the x-ray tube on the rotating gantry assembly becomes challenging. That is, the x-ray tube must be affixed to the gantry in such a fashion so as to withstand the forces applied thereto in a 40+ g load environment and prevent gantry-load direction displacement that would result in unacceptable image quality due to focal spot motion. However, the tube cannot be over-constrained, as over-constraint of the tube can result in (1) the creation of high loads internal to the tube casing structure and insert components that might result in deformation of these components responsive to the gantry rotation and to thermal displacements and growth in the tube that occur as the tube heats up during usage, and (2) the generation of unwanted motion of the focal spot in unintended directions. While flexible attachments such as o-rings, gaskets, or bushings/shim have traditionally been employed for joining the x-ray tube casing and insert to prevent over-constraint, it is recognized that such connection mechanisms may not be suitable for use in a 40+ g load environment, and present additional manufacturing challenges.

Therefore, it would be desirable to provide a system and method for mounting an x-ray tube on a CT gantry operating in a high g-load environment that provides for displacement control of the x-ray tube by limiting displacement of the tube in the gantry-load direction while allowing some flexibility to accommodate thermal displacements in the tube, so as to keep the structure from becoming over-constrained. It would also be desirable for such a system and method to reduce focal spot motion due to x-ray tube structure thermal displacements and/or over-constraint, provide for ease of installation without the use of shims or bushings, provide proper gantry-load direction support for high g-load applications, and reduce internal x-ray tube casing structure bolt loads.

BRIEF DESCRIPTION OF THE INVENTION

The invention is a directed method and apparatus for mounting an x-ray tube on a CT gantry assembly for use in high g-load applications. The method and apparatus provide for displacement control of the x-ray tube by limiting displacement of the tube in the gantry-load direction while allowing some flexibility to accommodate thermal displacements in the tube, so as to keep the structure from becoming over-constrained.

In accordance with one aspect of the invention, a CT system includes a rotatable gantry having an opening to receive an object to be scanned and an x-ray tube mounted on the rotatable gantry and configured to project a beam of x-rays toward the object, the x-ray tube comprising a casing including a plurality of bearing strut connections formed thereon. The CT system also includes a detector array mounted on the rotatable gantry opposite from the x-ray tube to receive x-rays attenuated through the object and a mounting structure configured to mount the x-ray tube on the rotatable gantry, with the mounting structure further including base plates having a plurality of bolt holes formed therein to receive bolts for securing the base plates to the rotatable gantry, each of the base plates including a plurality of bearing strut connections formed thereon. The mounting structure also includes a plurality of spherical bearing struts mechanically coupling the x-ray tube to the base plates, the plurality of spherical bearing struts each having a first end secured in a respective bearing strut connection of the x-ray tube casing and a second end secured in a respective bearing strut connection of the base plates. The plurality of spherical bearing struts are configured to constrain a gantry-load direction displacement of the x-ray tube and enable rotation and displacement of the x-ray tube around at least one axis of rotation or in one direction other than a gantry load direction, so as to accommodate thermal displacements in the x-ray tube created during operation thereof In accordance with another aspect of the invention, a method for mounting an x-ray tube on a rotatable gantry of a CT imaging system includes providing a pair of base plates each having a plurality of bolt holes formed therein and each including a plurality of bearing strut connections formed thereon, providing an x-ray tube comprising a casing having a plurality of bearing strut connections formed thereon, and mechanically coupling the x-ray tube to the pair of base plates by way of a plurality of spherical bearing struts, with each of the plurality of bearing struts including a pair of spherical bearings thereon positioned at opposing ends of the spherical bearing strut that are secured within the bearing strut connections of the x-ray tube casing and the base plates. The method also includes bolting the pair of base plates to the rotatable gantry so as to mount the x-ray tube on the rotatable gantry. In mechanically coupling the x-ray tube to the pair of base plates, the plurality of spherical bearing struts constrain a gantry-load direction displacement of the x-ray tube and enable rotation and displacement of the x-ray tube around at least one axis of rotation or in one direction other than the gantry load direction, so as to accommodate thermal displacements in the x-ray tube created during operation thereof.

In accordance with yet another aspect of the invention, a mounting structure for mounting an x-ray tube on a rotatable gantry of a CT imaging system includes a pair of base plates each having a plurality of bolt holes formed therein to receive bolts for securing the base plates to the rotatable gantry, with each of the base plates including a plurality of bearing strut connections formed thereon. The mounting structure also includes a plurality of spherical bearing struts mechanically coupling the x-ray tube to the base plates, with each of the plurality of spherical bearing struts further including a pair of spherical bearings, a pair of struts each comprising a first end configured to secure a respective spherical bearing therein and a second end opposite the first end, and a dual threaded turnbuckle configured to mate with the second end of each of the struts so as to mechanically couple the pair of struts together. One of the pair of spherical bearings on each spherical bearing strut is secured in a respective bearing strut connection of a respective base plate the other of the pair of spherical bearings on each spherical bearing strut is secured in a bearing strut connection formed on an outer casing of the x-ray tube.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy.

The invention will be described with respect to a "third generation" CT scanner, but is equally applicable with other CT systems.

Figure 1:
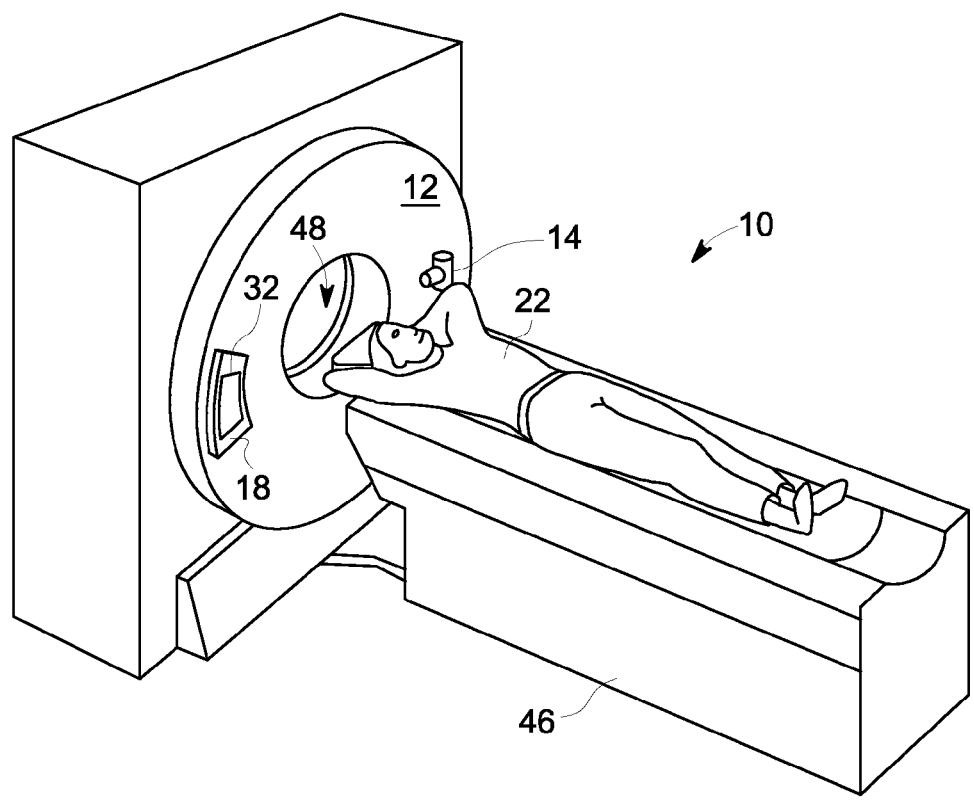
FIG. 1 is a pictorial view of a CT imaging system that can benefit from incorporation of an embodiment of the present invention.
Figure 2:
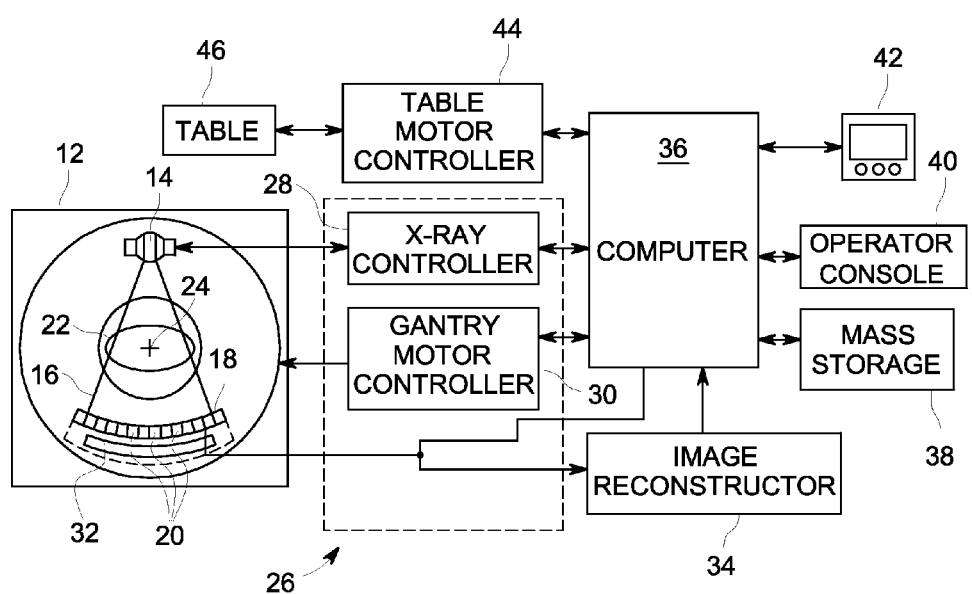
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 (i.e., x-ray tube 14) that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
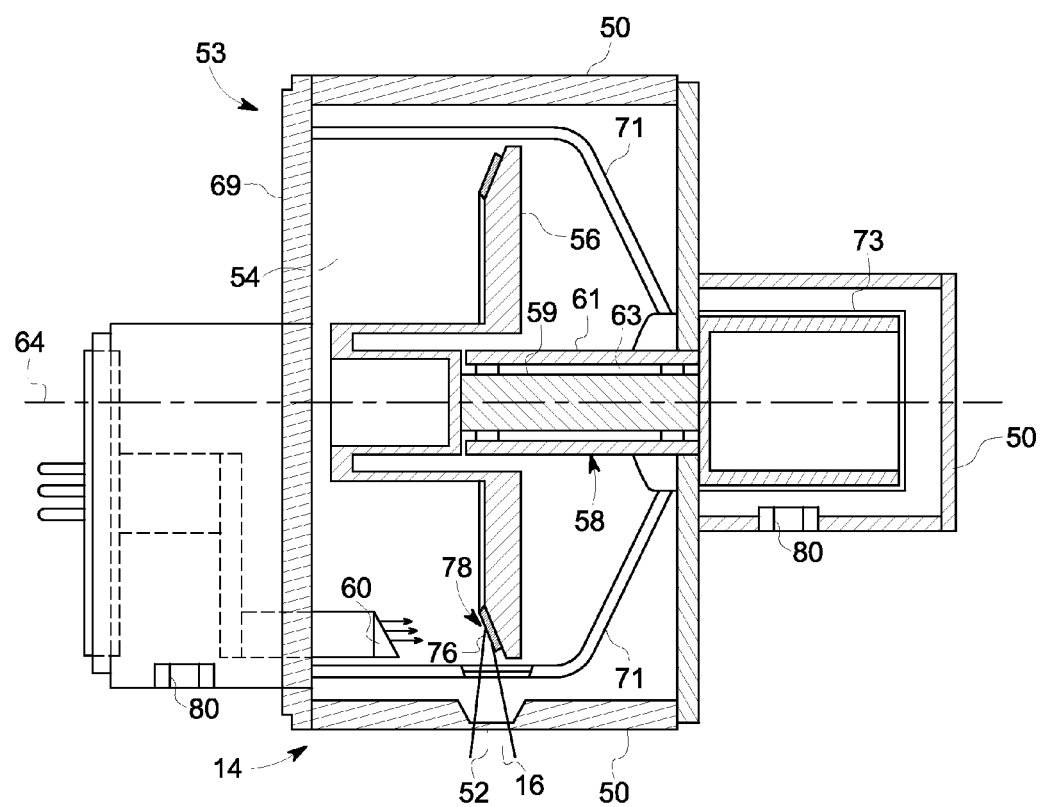
FIG. 3 is a cross-sectional view of an x-ray tube usable with the CT imaging system of FIGS. 1 and 2.

Referring now to FIG. 3, a cross-sectional view of an x-ray tube 14 that could be mounted on the gantry 12 of CT system 10 is illustrated that can benefit from incorporation of an embodiment of the invention—although it is recognized that embodiments of the invention are not meant to be limited to an x-ray tube having the specific structure of x-ray tube 14 and that other x-ray tube structures are considered to be within the scope of the invention. The x-ray tube 14 includes a casing 50 having a radiation emission passage 52 formed therein. The casing 50 partially houses an insert 53 that encloses vacuum 54 having an anode target (or rotating subsystem) 56, a bearing assembly 58, a cathode 60, and a rotor 62, with the anode target 56 being rotated at a high rate of speed about a centerline 64 (or rotating axis of the shaft).

As shown in FIG. 3, bearing assembly 58 includes a stationary inner shaft 59 rollingly engaged with a rotatable outer shaft 61, and with a gap 63 therebetween.

The x-ray tube 14 also includes a support plate 69, a frame 71, and a rotor can 73, in part forming vacuum 54 in which the target 56, outer shaft 61, and rotor 62 of the rotating subsystem are positioned. Inner shaft 59, support plate 69, frame 71, and rotor can 73 are hard-connected (i.e., physically hard-attached to one another by weld, braze or by a combination of both).

According to an embodiment of the invention, and as shown in FIG. 3, the casing 50 of x-ray tube 14 includes a plurality of bearing strut connections 80 formed thereon that provide for mounting of the x-ray tube 14 to the gantry 12, as will be explained in further detail below. In one embodiment, the plurality of bearing strut connections 80 formed on the x-ray tube casing 50 are integrally formed onto the casing 50 (i.e., cast as part of the casing 50) so as to increase the structural strength thereof. According to an exemplary embodiment of the invention, bearing strut connections 80 are formed on casing 50 at what are generally described as the "four corners" of the x-ray tube casing 50. That is, a pair of bearing strut connections 80 are formed on casing 50 generally adjacent to cathode 60—and generally on opposing sides of cathode 60—and a pair of bearing strut connections 80 are formed on casing 50 generally adjacent to rotor can 73—and generally on opposing sides of rotor can 73 (as is best illustrated in FIG. 4).

Referring still to FIG. 3, in operation of x-ray tube 14, x-rays 16 are produced when high-speed electrons from a primary electron beam are suddenly decelerated when directed from the cathode 60 to the target 56 via a potential difference therebetween. In high voltage CT applications, the potential difference between the cathode 60 and target 56 may be, for example, 60 thousand volts (keV) and up to 140 keV or more. In other applications, the potential difference may be lower. The electrons impact a material layer or target focal track 76 at a focal spot or point 78 and x-rays 16 emit therefrom. The point of impact at focal point 78 is typically referred to in the industry as the focal spot. The x-rays 16 emit through the radiation emission passage 52 toward a detector array, such as detector array 18 of FIGS. 1 and 2. In high voltage CT applications, to avoid overheating target 56 from the electrons, target 56 is rotated at a high rate of speed about the centerline 64 at, for example, 75-250 Hz. In lower voltage or power applications the target 56 may remain stationary.

With respect to CT imaging system 10 and x-ray tube 14, it is recognized that CT imaging systems have recently required increasingly higher gantry rotational speeds that result in high g-loads on the x-ray tube 14. In such high speed, high g-load systems, the gantry load forces that might cause x-ray tube 14 displacement in the gantry-load direction are magnified, and it is recognized that such displacement in the gantry-load direction is undesirable because such displacements results in motion of focal spot 78 can that result in unacceptable image quality. Therefore, the x-ray tube 14 must be properly constrained to gantry 12 in order to limit gantry-load directional displacement. It is recognized, however, that simply rigidly constraining the x-ray tube 14 to the gantry 12 can result in an "over-constrained" loading condition that generates high loads internal to the casing 50—with such loads being due to thermal loading from thermal growth (caused by differential growth of various x-ray tube components of differing materials that occur during high temperature operation of the x-ray tube 14) and due to structural loading from the high-speed rotation of gantry 12. In an over-constrained condition, the thermal loading resulting from thermal growth can cause casing 50 and insert 53 components to deform as the x-ray tube 14 heats up during usage, which can further result in unwanted motion of the focal spot 78.

Figure 4:
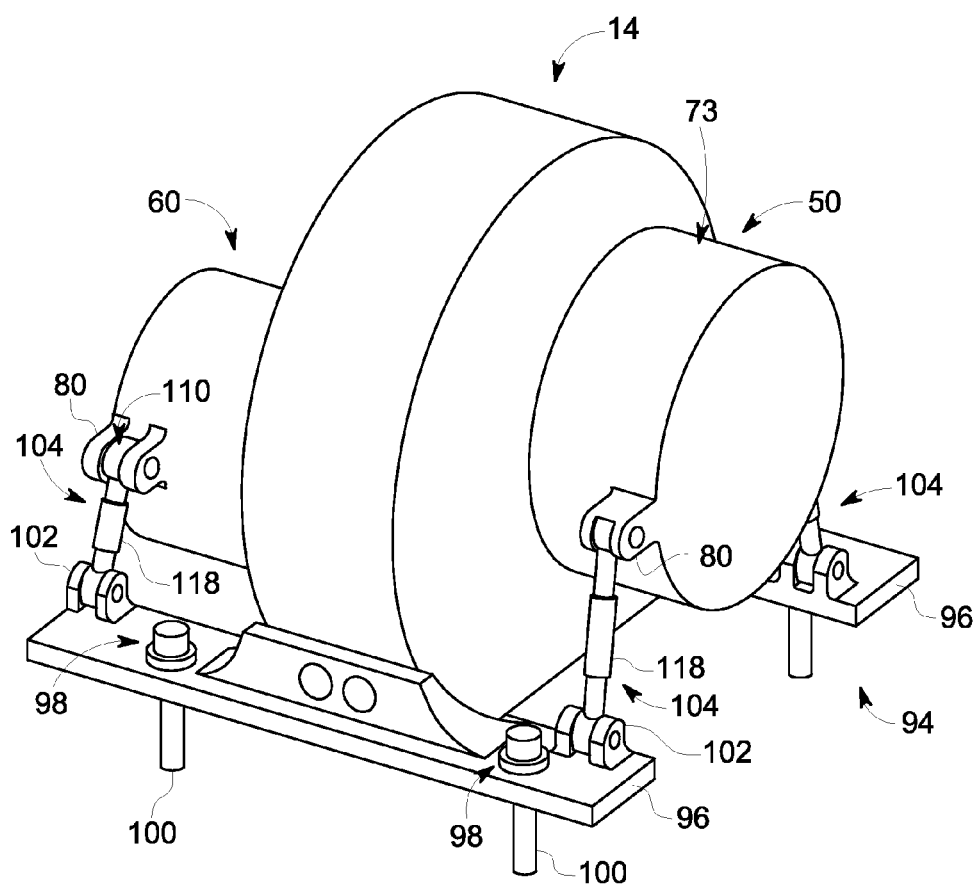
FIGS. 4-6 are views of a mounting structure for mounting an x-ray tube on a rotatable CT gantry according to an embodiment of the invention.
Figure 5:
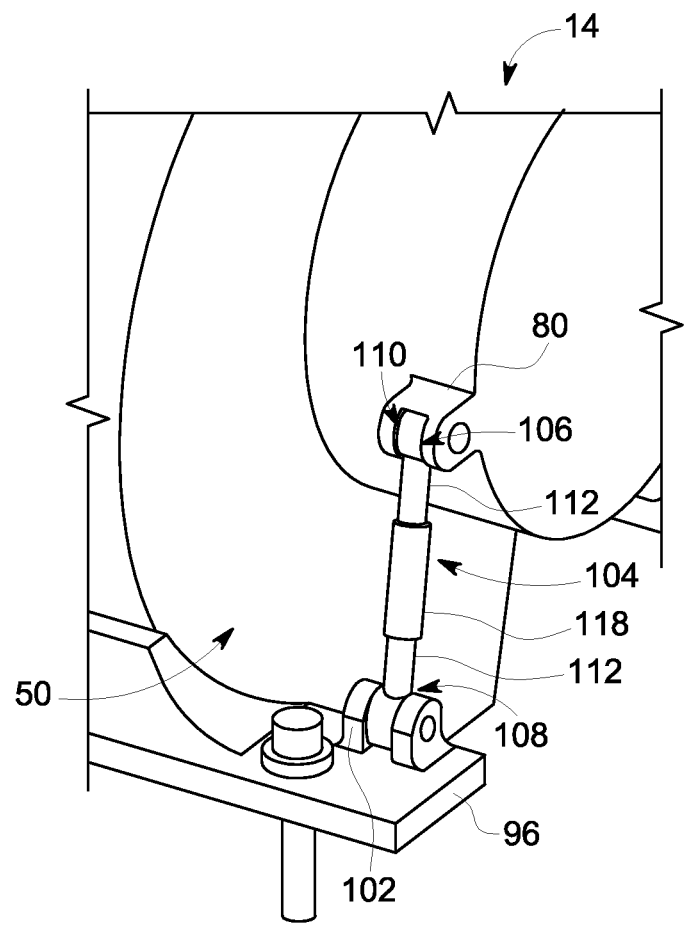
Figure 6:
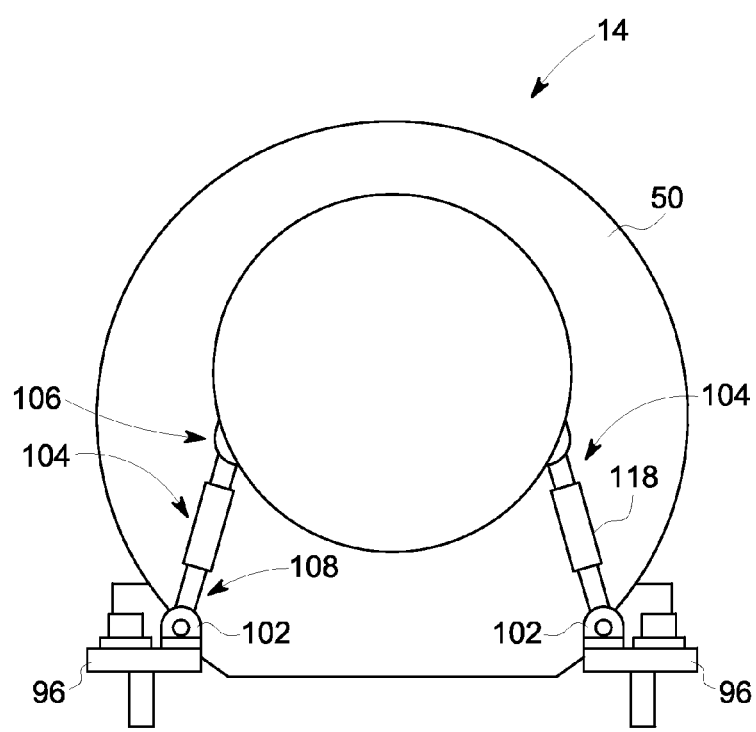

Referring now to FIGS. 4-6, various views of a mounting structure 94 for mounting x-ray tube 14 to gantry 12 of CT imaging system 10 are shown according to an embodiment of the invention. The mounting structure 94 is configured to constrain a gantry-load direction displacement of the x-ray tube 14 while still enabling selective rotation and displacement of the x-ray tube around at least one axis of rotation or in one direction other than a gantry load direction, so as to accommodate thermal displacements in the x-ray tube created during operation thereof and structural loading from the high-speed rotation of gantry 12.

As shown in FIGS. 4-6, mounting structure 94 includes a pair of base plates 96 each having a plurality of bolt holes 98 formed therein to receive bolts 100 for securing the base plates 96 to the rotatable gantry 12. Each of the base plates 96 also includes a plurality of bearing strut connections 102 formed thereon. On each base plate 96, a bearing strut connection 102 is formed generally on each of opposing ends of the baseplate. In one embodiment, the bearing strut connections 102 formed on each of the base plates 96 are integrally formed into the base plates 96, so as to increase the structural strength thereof.

Also included in mounting structure 94 is a plurality of spherical bearing struts 104 that mechanically couple the x-ray tube 14 to the base plates 96. As shown in FIGS. 4-6, the plurality of spherical bearing struts 104 each generally have a first end 106 secured in a respective bearing strut connection 80 of the x-ray tube casing 50 and a second end 108 secured in a respective bearing strut connection 102 of the base plates 96.

According to one embodiment, four spherical bearing struts 104 are provided in mounting structure 94 for mechanically coupling the x-ray tube 14 to the base plates 96, with the spherical bearing struts 104 being arranged to connect at "four corners" of the x-ray tube casing 50, such that the x-ray tube 14 is held radially on the gantry 12. That is, on each base plate 96, second ends 108 of a pair of spherical bearing struts 104 are secured to the bearing strut connections 102 formed on generally opposite ends of the base plate 96, and first ends 106 of the spherical bearing struts 104 are secured to the bearing strut connections 80 formed on the x-ray tube casing 50, with the first ends 106 of two spherical bearing struts 104 being secured to bearing strut connections 80 formed on casing 50 generally adjacent to cathode 60—and generally on opposing sides of cathode 60—and the first ends 106 of two spherical bearing struts 104 being secured to bearing strut connections 80 formed on casing 50 generally adjacent to rotor can 73—and generally on opposing sides of rotor can 73 (see FIGS. 3 and 4).

In mounting the x-ray tube 14 to the base plates 96 via spherical bearing struts 104 arranged to connect at "four corners" of the x-ray tube casing 50, the plurality of spherical bearing struts 104 are thus arranged to "straddle-mount" the x-ray tube 14 to the rotatable gantry 12. That is, by supporting/affixing the x-ray tube 14 to gantry 12 at a first end of the tube and an opposing second end of the tube (i.e., front and rear ends of the tube) with the plurality of spherical bearing struts 104, a solid support or "straddle" is provided to mount—i.e., "straddle-mount"—the tube to the gantry 12.

Figure 7:
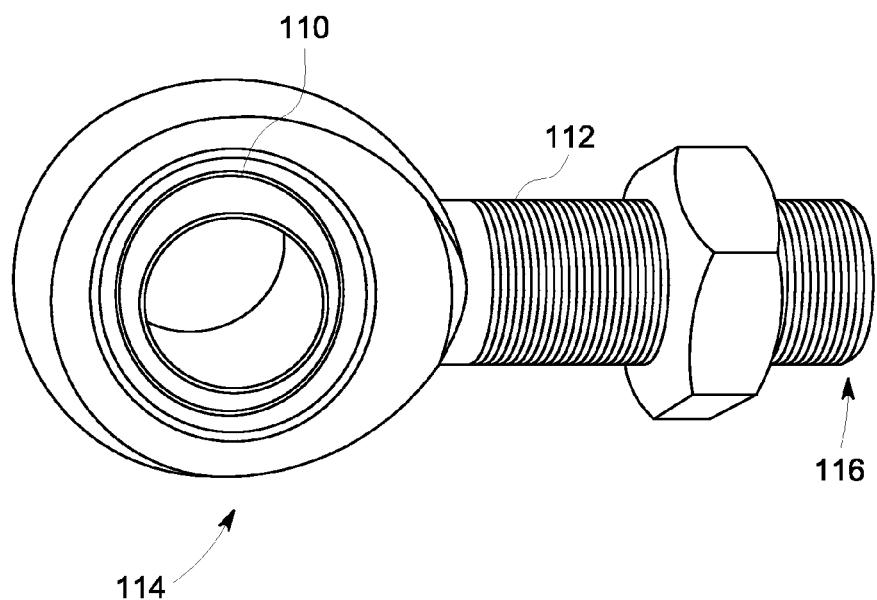
FIG. 7 is a detailed view of a portion of a spherical bearing strut for use in the mounting structure shown in FIGS. 4-6.

With respect to the construction of each spherical bearing strut 104, each spherical bearing strut 104 includes a pair of spherical bearings 110 and a pair of struts 112, as can best be seen in the detailed view of FIG. 7. Each spherical bearing 110 is housed within a respective strut 112. Each strut 112 has a first end 114 configured to secure a respective spherical bearing 110 therein and a second end 116 opposite the first end, with the second end being formed as a threaded attachment section, for example. According to one embodiment, each of the pair of struts 112 may have a preload set therein that can be provided prior to attachment of the spherical bearing strut 104 to x-ray tube 14 and base plates 96.

As shown in FIGS. 4-6, each of the plurality of spherical bearings struts 104 also includes a dual threaded turnbuckle 118 that is configured to mate with the second end 116 of each of the struts 112 so as to mechanically couple the pair of struts 112 together. By coupling struts 112 together via threaded turnbuckle 118, a spherical bearings strut 104 is thus formed having spherical bearings 110 securable on both ends 106, 108 to bearing strut connections 80, 102 of the x-ray tube casing 50 and base plates 96, respectively.

Based on the construction of spherical bearing struts 104, and the securing of the spherical bearings 110 thereof in bearing strut connections 80, 102 of the x-ray tube casing 50 and base plates 96, the spherical bearing struts 104 are configured to constrain a gantry-load direction displacement of the x-ray tube 14, while enabling rotation and displacement of the x-ray tube 14 around at least one axis of rotation or in one direction other than a gantry-load direction, so as to accommodate thermal displacements in the x-ray tube 14 created during operation thereof and/or structural loading from the high-speed rotation of gantry 12. With respect to constraining a gantry-load direction displacement of the x-ray tube 14, the plurality of spherical bearing struts 104 are configured to constrain gantry-load direction displacement of the x-ray tube 14 at loads of 40 g's or more, so as to minimize motion of a focal spot 78 generated on the anode target 56 at high speeds of gantry rotation. With respect to enabling rotation around at least one axis of rotation, the movement of the spherical bearings 110 within respective bearing strut connections 80, 102 allows up to three rotational degrees of freedom for accommodating displacement of x-ray tube 14 (i.e., displacement other than gantry-load direction displacement).

Figure 8:
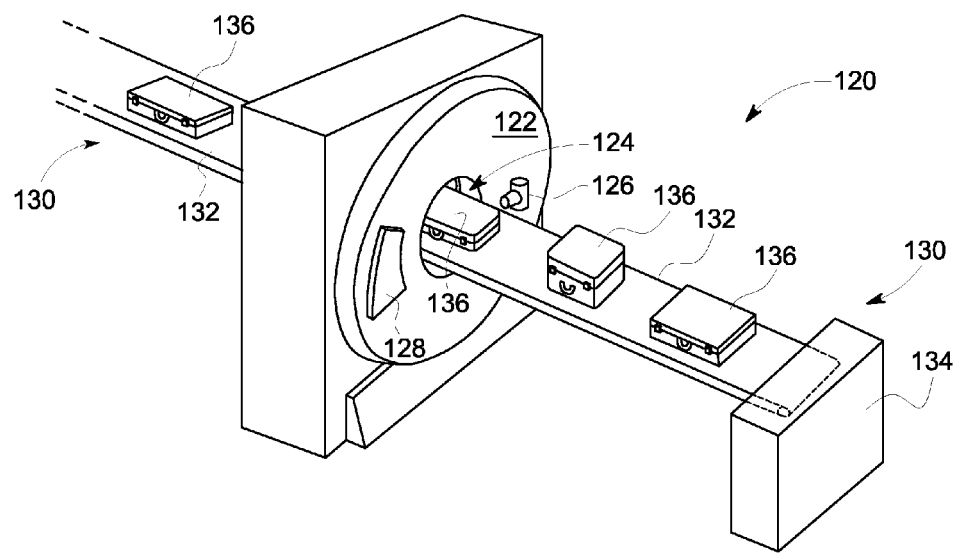
FIG. 8 is a pictorial view of a CT system for use with a non-invasive package inspection system that can benefit from incorporation of an embodiment of the present invention.

Referring now to FIG. 8, package/baggage inspection system 120 includes a rotatable gantry 122 having an opening 124 therein through which packages or pieces of baggage may pass. The rotatable gantry 122 houses a high frequency electromagnetic energy source 126 (i.e., x-ray tube 126) as well as a detector assembly 128. A conveyor system 130 is also provided and includes a conveyor belt 132 supported by structure 134 to automatically and continuously pass packages or baggage pieces 136 through opening 124 to be scanned. Objects 136 are fed through opening 124 by conveyor belt 132, imaging data is then acquired, and the conveyor belt 132 removes the packages 136 from opening 124 in a controlled and continuous manner. As a result, postal inspectors, baggage handlers, and other security personnel may non-invasively inspect the contents of packages 136 for explosives, knives, guns, contraband, etc.

According to one embodiment, the x-ray tube 126 of package/baggage inspection system 120 is mounting on rotatable gantry by way of a mounting structure 94 such as shown in FIGS. 4-6. The mounting structure 94 enables operation of package/baggage inspection system 120 at high speeds that might induce loads of 40 g's or more on x-ray tube 126—if operation of the system in such a manner is desired. In doing so, the mounting structure 94 prevent displacements of the x-ray tube 126 in a gantry-load direction, while providing for some displacement of the tube in directions other than the gantry-load direction, so as to accommodate thermal growth and thereby reduce deformation of components within the tube and maintain a desirable image quality (by minimizing focal spot movement).

Beneficially, embodiments of the invention thus provide a mounting structure 94 utilized to mount an x-ray tube 14 to a CT rotating gantry 12 that allows for selective displacement control and maintains image quality. Spherical bearing struts 104 are provided in mounting mechanism 94 that prevent displacement of the x-ray tube 14 in a gantry-load direction, while preventing the x-ray tube from becoming over-constrained based on the spherical bearing struts 104 allowing up to three rotational degrees of freedom. The rotational degrees of freedom provided by spherical bearing struts 104 allow some displacement in directions other than the gantry-load direction so as to accommodate thermal growth and greatly reduce resulting deformation. Because some displacement is allowed, supports and connection in/of the x-ray tube 14 may have reduced stiffness and overall loads in the x-ray tube 14 may be reduced. Reduced loads may allow for smaller and fewer bolts to be used throughout the x-ray tube 14 and its mounting structure 94, and may allow for higher safety factors.

Therefore, according to one embodiment of the invention, a CT system includes a rotatable gantry having an opening to receive an object to be scanned and an x-ray tube mounted on the rotatable gantry and configured to project a beam of x-rays toward the object, the x-ray tube comprising a casing including a plurality of bearing strut connections formed thereon. The CT system also includes a detector array mounted on the rotatable gantry opposite from the x-ray tube to receive x-rays attenuated through the object and a mounting structure configured to mount the x-ray tube on the rotatable gantry, with the mounting structure further including base plates having a plurality of bolt holes formed therein to receive bolts for securing the base plates to the rotatable gantry, each of the base plates including a plurality of bearing strut connections formed thereon. The mounting structure also includes a plurality of spherical bearing struts mechanically coupling the x-ray tube to the base plates, the plurality of spherical bearing struts each having a first end secured in a respective bearing strut connection of the x-ray tube casing and a second end secured in a respective bearing strut connection of the base plates. The plurality of spherical bearing struts are configured to constrain a gantry-load direction displacement of the x-ray tube and enable rotation and displacement of the x-ray tube around at least one axis of rotation or in one direction other than a gantry load direction, so as to accommodate thermal displacements in the x-ray tube created during operation thereof.

According to another embodiment of the invention, a method for mounting an x-ray tube on a rotatable gantry of a CT imaging system includes providing a pair of base plates each having a plurality of bolt holes formed therein and each including a plurality of bearing strut connections formed thereon, providing an x-ray tube comprising a casing having a plurality of bearing strut connections formed thereon, and mechanically coupling the x-ray tube to the pair of base plates by way of a plurality of spherical bearing struts, with each of the plurality of bearing struts including a pair of spherical bearings thereon positioned at opposing ends of the spherical bearing strut that are secured within the bearing strut connections of the x-ray tube casing and the base plates. The method also includes bolting the pair of base plates to the rotatable gantry so as to mount the x-ray tube on the rotatable gantry. In mechanically coupling the x-ray tube to the pair of base plates, the plurality of spherical bearing struts constrain a gantry-load direction displacement of the x-ray tube and enable rotation and displacement of the x-ray tube around at least one axis of rotation or in one direction other than the gantry load direction, so as to accommodate thermal displacements in the x-ray tube created during operation thereof.

According to yet another embodiment of the invention, a mounting structure for mounting an x-ray tube on a rotatable gantry of a CT imaging system includes a pair of base plates each having a plurality of bolt holes formed therein to receive bolts for securing the base plates to the rotatable gantry, with each of the base plates including a plurality of bearing strut connections formed thereon. The mounting structure also includes a plurality of spherical bearing struts mechanically coupling the x-ray tube to the base plates, with each of the plurality of spherical bearing struts further including a pair of spherical bearings, a pair of struts each comprising a first end configured to secure a respective spherical bearing therein and a second end opposite the first end, and a dual threaded turnbuckle configured to mate with the second end of each of the struts so as to mechanically couple the pair of struts together. One of the pair of spherical bearings on each spherical bearing strut is secured in a respective bearing strut connection of a respective base plate the other of the pair of spherical bearings on each spherical bearing strut is secured in a bearing strut connection formed on an outer casing of the x-ray tube.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computed tomography (CT) system comprising:
 a rotatable gantry having an opening to receive an object to be scanned;
 an x-ray tube mounted on the rotatable gantry and configured to project a beam of x-rays toward the object, the x-ray tube comprising a casing including a plurality of bearing strut connections formed thereon;
 a detector array mounted on the rotatable gantry opposite from the x-ray tube to receive x-rays attenuated through the object; and
 a mounting structure configured to mount the x-ray tube on the rotatable gantry, the mounting structure comprising:
  base plates having a plurality of bolt holes formed therein to receive bolts for securing the base plates to the rotatable gantry, each of the base plates including a plurality of bearing strut connections formed thereon; and
  a plurality of spherical bearing struts mechanically coupling the x-ray tube to the base plates, the plurality of spherical bearing struts each having a first end secured in a respective bearing strut connection of the x-ray tube casing and a second end secured in a respective bearing strut connection of the base plates;
  wherein the plurality of spherical bearing struts are configured to constrain a gantry-load direction displacement of the x-ray tube and enable rotation and displacement of the x-ray tube around at least one axis of rotation or in one direction other than a gantry load direction, so as to accommodate thermal displacements in the x-ray tube created during operation thereof.

2. The CT system of claim 1 wherein each of the plurality of spherical bearing struts comprises:
 a pair of spherical bearings;
 a pair of struts each comprising a first end configured to secure a respective spherical bearing therein and a second end opposite the first end; and
 a dual threaded turnbuckle configured to mate with the second end of each of the struts so as to mechanically couple the pair of struts together.

3. The CT system of claim 1 wherein each of the pair of struts has a preload set therein.

4. The CT system of claim 1 wherein the plurality of bearing strut connections formed on the x-ray tube casing are integrally formed into the casing.

5. The CT system of claim 1 wherein the plurality of bearing strut connections formed on each of the base plates are integrally formed into the base plates.

6. The CT system of claim 1 wherein the x-ray tube further comprises:
 an insert positioned within the casing that surrounds a vacuum chamber;
 a rotating target positioned within the vacuum chamber and comprising a focal track; and
 a cathode positioned across from the rotating target within the vacuum chamber and configured to shoot a stream of electrons toward a focal spot on focal track;
 wherein the plurality of spherical bearing struts, in enabling rotation and displacement of the x-ray tube around at least one axis of rotation or in one direction other than the gantry load direction so as to accommodate thermal displacements in the x-ray tube, are configured to minimize motion of the focal spot.

7. The CT system of claim 6 wherein the plurality of spherical bearing struts are secured to the x-ray tube bearing strut connections so as to straddle-mount the rotating target in mounting the x-ray tube to the rotatable gantry.

8. The CT system of claim 7 wherein the plurality of spherical bearing struts comprises four spherical bearing struts, with the four spherical bearing struts being arranged to connect to the plurality of bearing strut connections of the x-ray tube casing generally at four opposing corners of the x-ray tube casing and such that the four opposing corners are mounted radially on the gantry.

9. The CT system of claim 1 wherein the plurality of spherical bearing struts are configured to allow three rotational degrees of freedom, such that motion of the spherical bearings and associated struts accommodate thermal displacements.

10. The CT system of claim 1 wherein the plurality of spherical bearing struts are configured to constrain gantry-load direction displacement of the x-ray tube at loads of 40 g's or more.

11. A method for mounting an x-ray tube on a rotatable gantry of a computed tomography (CT) imaging system, the method comprising:
 providing a pair of base plates having a plurality of bolt holes formed therein, each of the pair of base plates including a plurality of bearing strut connections formed thereon;
 providing an x-ray tube comprising a casing having a plurality of bearing strut connections formed thereon;
 mechanically coupling the x-ray tube to the pair of base plates by way of a plurality of spherical bearing struts, each of the plurality of bearing struts including a pair of spherical bearings thereon positioned at opposing ends of the spherical bearing strut that are secured within the bearing strut connections of the x-ray tube casing and the base plates; and
 bolting the pair of base plates to the rotatable gantry so as to mount the x-ray tube on the rotatable gantry;
 wherein, in mechanically coupling the x-ray tube to the pair of base plates, the plurality of spherical bearing struts constrain a gantry-load direction displacement of the x-ray tube and enable rotation and displacement of the x-ray tube around at least one axis of rotation or in one direction other than the gantry load direction, so as to accommodate thermal displacements in the x-ray tube created during operation thereof.

12. The method of claim 11 wherein providing the x-ray tube comprises providing an x-ray tube having a plurality of bearing strut connections integrally cast into the casing.

13. The method of claim 11 wherein each of the plurality of spherical bearing struts comprises:
   a pair of spherical bearings;
   a pair of struts each comprising a first end configured to secure a respective spherical bearing therein and a second end opposite the first end; and
   a dual threaded turnbuckle configured to mate with the second end of each of the struts so as to mechanically couple the pair of struts together.

14. The method of claim 13 wherein, in mechanically coupling the x-ray tube to the pair of base plates, the plurality of spherical bearing struts allow three rotational degrees of freedom, such that motion of the spherical bearings and associated struts accommodate thermal displacements.

15. The method of claim 11 wherein mechanically coupling the x-ray tube to the pair of base plates comprises straddle-mounting the x-ray tube to the pair of base plates.

16. The method of claim 15 wherein straddle-mounting the x-ray tube to the pair of base plates comprises securing four respective spherical bearing struts to four generally opposing corners of the x-ray tube casing, such that the four opposing corners are mounted to the pair of base plates.

17. A mounting structure for mounting an x-ray tube on a rotatable gantry of a computed tomography (CT) imaging system, the mounting structure comprising:
   a pair of base plates each having a plurality of bolt holes formed therein to receive bolts for securing the base plates to the rotatable gantry, each of the base plates including a plurality of bearing strut connections formed thereon; and
   a plurality of spherical bearing struts mechanically coupling the x-ray tube to the base plates, each of the plurality of spherical bearing struts comprising:
      a pair of spherical bearings;
      a pair of struts each comprising a first end configured to secure a respective spherical bearing therein and a second end opposite the first end; and
      a dual threaded turnbuckle configured to mate with the second end of each of the struts so as to mechanically couple the pair of struts together;
      wherein one of the pair of spherical bearings on each spherical bearing strut is secured in a respective bearing strut connection of a respective base plate the other of the pair of spherical bearings on each spherical bearing strut is secured in a bearing strut connection formed on an outer casing of the x-ray tube.

18. The mounting structure of claim 17 wherein the plurality of spherical bearing struts are configured to constrain a gantry-load direction displacement of the x-ray tube while accommodating thermal displacements in the x-ray tube created during operation thereof.

19. The mounting structure of claim 18 wherein the spherical bearing in each of the plurality of spherical bearing struts provide three rotational degrees of freedom to accommodate the thermal displacements in the x-ray tube.

20. The mounting structure of claim 17 wherein the plurality of spherical bearing struts are configured to constrain gantry-load direction displacement of the x-ray tube at loads of 40 g's or more.

\* \* \* \* \*